United States Patent
Guadagno

(10) Patent No.: US 9,759,682 B2
(45) Date of Patent: Sep. 12, 2017

(54) APPLICATOR COMB FOR GEL ELECTROPHORESIS

(71) Applicant: True Health Diagnostics LLC, Frisco, TX (US)

(72) Inventor: Philip Guadagno, Vashon Island, WA (US)

(73) Assignee: True Health IP LLC, Frisco, TX (US)

( * ) Notice: Subject to any disclaimer, the term of this patent is extended or adjusted under 35 U.S.C. 154(b) by 477 days.

(21) Appl. No.: 14/455,612

(22) Filed: Aug. 8, 2014

(65) Prior Publication Data

US 2016/0041123 A1 Feb. 11, 2016

Related U.S. Application Data

(60) Provisional application No. 61/864,336, filed on Aug. 9, 2013, provisional application No. 61/979,795, filed on Apr. 15, 2014.

(51) Int. Cl.
*G01N 27/453* (2006.01)
*G01N 27/447* (2006.01)
*G01N 1/00* (2006.01)

(52) U.S. Cl.
CPC . *G01N 27/44743* (2013.01); *G01N 2001/002* (2013.01)

(58) Field of Classification Search
CPC ......... G01N 2001/002; G01N 2001/02; G01N 2001/10; G01N 2001/1056; G01N 27/44756
See application file for complete search history.

(56) References Cited

U.S. PATENT DOCUMENTS

| 5,284,565 A | 2/1994 | Chu et al. |
|---|---|---|
| 5,972,188 A * | 10/1999 | Rice ................. G01N 27/44743 204/456 |
| 6,544,395 B1 | 4/2003 | Merchant |
| 2012/0052594 A1 | 3/2012 | Guadagno et al. |

FOREIGN PATENT DOCUMENTS

| EP | 1197750 A2 | 4/2002 |
|---|---|---|
| EP | 1338893 A2 | 8/2003 |
| WO | 98/00706 A1 | 1/1998 |
| WO | 99/54721 A1 | 10/1999 |
| WO | WO2013/181267 | 12/2013 |

OTHER PUBLICATIONS

International Search Report and Written Opinion dated Mar. 2, 2015 for International Application No. PCT/US14/50397.

* cited by examiner

*Primary Examiner* — Alexander Noguerola
(74) *Attorney, Agent, or Firm* — Perkins Coie LLP

(57) ABSTRACT

A fluid applicator device includes an applicator body having a surface that is generally planar. A plurality of aligned applicator teeth extend from said applicator body. Each applicator tooth extends longitudinally from said applicator body along a length from a base of the applicator tooth proximate to the applicator body to a tip of the applicator tooth distal to the applicator body. At least one applicator tooth of the plurality of aligned applicator teeth has a width that is greater at the base than at the tip. A method for depositing a liquid sample on a substrate using the fluid applicator device is also disclosed.

26 Claims, 3 Drawing Sheets

APPLICATOR COMB FOR GEL ELECTROPHORESIS

This application claims the benefit of U.S. Provisional Patent Application Ser. No. 61/864,336 filed Aug. 9, 2013 and U.S. Provisional Application Ser. No. 61/979,795 filed Apr. 15, 2014, both of which are hereby incorporated by reference in their entirety.

FIELD

The invention is related to the field of electrophoretic analysis of biological specimens, including the application of biological samples to an electrophoresis plate. More specifically, the present invention is directed to a fluid applicator device and a method for depositing a liquid sample on a substrate utilizing the fluid applicator device for in situ electrophoretic analysis of biological specimens.

BACKGROUND

In clinical laboratory practice, various techniques, such as electrophoresis, are used to apply samples to substrates for separation and analysis. Electrophoresis in general is the voltage-driven migration of suspended and/or colloidal particles in a liquid or a gel, due to the effect of a potential difference across immersed electrodes. In many devices that use electrophoresis, the strategy is to apply a sample just to the surface of a substrate, then apply a voltage to separate the components of the sample. This strategy is used in techniques like immunofixation-based electrophoresis and two-dimensional electrophoresis.

Electrophoresis is often used in the study of proteins and colloidal particles from biological samples, such as evaluation of lipoparticles and lipoproteins. In immunofixation methods, such as described in U.S. Patent Application Publication No. 2012/0052594, which is hereby incorporated herein by reference in its entirety, a biological sample (e.g., serum) is applied to a substrate and the components are electrophoresed. Anti-sera containing labeled antibodies that target specific components of the blood is applied to the substrate. The antibodies attach to their antigen targets, and the targets can be identified through some means of detecting the label.

In clinical applications, it is desirable to analyze many samples in parallel on the same substrate. This reduces the cost per sample analyzed and saves substantial time. High throughput instruments and devices, such as the SPIFE 3000 Assay instrument by Helena Laboratories, are made for this purpose.

High throughput instruments use an applicator comb to apply a series of samples in a single line on the substrate. Such an applicator comb, having a design using squared-off teeth, is described in U.S. Pat. No. 6,544,395, which is hereby incorporated by reference herein in its entirety.

There is a desire in the art to increase the number of samples per substrate to increase throughput and make the method more efficient. Increasing the number of teeth per applicator comb would accomplish this goal. However, increasing the number of teeth without a change in design is not effective due to reduced fluid control in the smaller tooth dimensions. Also, structural integrity is lost when the tooth width is reduced, making each tooth more easily deformable during manufacture and when in contact with sample reservoirs and the substrate.

Simply making the teeth smaller to accommodate more samples non-reproducibly reduces the amount of sample per tooth deposited/transferred, lowering the ability to detect target components of the sample after they have been separated. Additionally, variable sample deposition with increasing the number of teeth per applicator comb can cause lane contamination so that adjacent lane samples bleed into one another rendering the samples as unreliable for measurement.

In previous efforts to generate a greater sample density on the gel, the teeth were manufactured to be narrower. However, a direct reduction in size/geometry led to inconsistent liquid management and generally reduced liquid deposition. The volume of the liquid to be applied must be of sufficient volume to accommodate the sensitivity of the assay. The narrower tooth must therefore have the ability to both load appropriate volumes and unload those volumes in a controlled and reproducible fashion. A narrower tooth without additional surface to adsorb the liquid will result in the liquid droplet surface protruding too far from the surface of the tooth, increasing the necessary surface tension to hold the liquid droplet in place. The flash dimension of each tooth is insufficient to maintain surface tension of the liquid droplet to prevent premature liquid release if the tooth is too narrow and no other provision is made to hold the liquid.

The present invention is directed to overcoming these and other deficiencies in the art.

SUMMARY

One aspect of the present invention relates to a fluid applicator device including an applicator body having a surface that is generally planar. A plurality of aligned applicator teeth extend from said applicator body. Each applicator tooth extends longitudinally from said applicator body along a length from a base of the applicator tooth proximate to the applicator body to a tip of the applicator tooth distal to the applicator body. At least one applicator tooth of the plurality of aligned applicator teeth has a width that is greater at the base than at the tip.

Another aspect of the present invention relates to a method for depositing a liquid sample on a substrate comprising providing a fluid applicator device comprising an applicator body having a surface that is generally planar. A plurality of aligned applicator teeth extend from said applicator body. Each applicator tooth extends longitudinally from said applicator body along a length from a base of the applicator tooth proximate to the applicator body to a tip of the applicator tooth distal to the applicator body. At least one applicator tooth of the plurality of aligned applicator teeth has a width that is greater at the base than at the tip. Each tooth of the applicator device is inserted into and removed from a supply volume of sample, thereby retaining a test volume of sample on each tooth. At least a portion of the test volume of sample is deposited onto a substrate by contacting the tips of the plurality of teeth of the fluid applicator device with the substrate.

The present invention provides improved performance for sample loading, transfer, and deposition. The invention offers improvements in liquid management, including improved control of liquid flow during sample deposition. The invention further provides an applicator with a higher number of applicator teeth without loss of resolution, sensitivity or fluid transfer control. The higher number of applicator teeth improves efficiency in high throughput laboratories.

DETAILED DESCRIPTION

The present invention relates to a fluid applicator device and a method for depositing a liquid sample on a substrate using the fluid applicator device.

One aspect of the present invention relates to a fluid applicator device including an applicator body having a surface that is generally planar. A plurality of aligned applicator teeth extend from said applicator body. Each applicator tooth extends longitudinally from said applicator body along a length from a base of the applicator tooth proximate to the applicator body to a tip of the applicator tooth distal to the applicator body. At least one applicator tooth of the plurality of aligned applicator teeth has a width that is greater at the base than at the tip.

Figure 1:
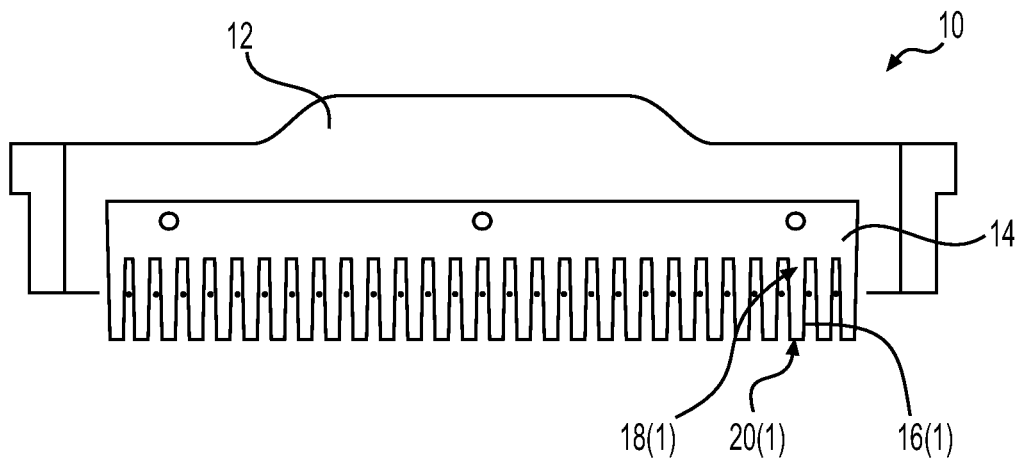
FIG. 1 is a side view of an embodiment of the fluid applicator device of the present invention.

FIG. 1 shows a side view of one embodiment of a fluid applicator device 10 of the present invention. Fluid applicator device 10 may be used for the parallel application of samples to a gel substrate for gel electrophoresis applications. The fluid applicator device 10 as described herein may be used with any suitable gel electrophoresis system and/or method. Such gel electrophoresis systems and methods include, for example, those described in WO 2013/181267 and U.S. Patent Application Publication No. 2012/0052594, each of which is hereby incorporated by reference in its entirety.

For instance, the fluid applicator device 10 may be used in carrying out the step of depositing a sample in a receiving well of an electrophoretic gel as part of a method for performing electrophoresis. An exemplary method may be carried out with in-situ calibration and involve combining a volume of a test sample with a volume or quantity of a calibrating sample to form a final volume, in which the volume or quantity of the calibrating sample includes a known concentration of a calibrator and the final volume includes a known ratio of test sample to calibrating sample. The method also includes depositing a loading fraction in a receiving well of an electrophoretic gel, in which the loading fraction is a fraction of the final volume and separating the loading fraction along a common separation lane of the electrophoretic gel such that components of the test sample and the calibrator are separated from one another along the common separation lane. The method also includes detecting the calibrator and separated components of test sample within the common separation lane and measuring the level of the calibrator and separated components of the test sample based on the detecting, thereby performing electrophoresis with in-situ calibration.

As a further example, the fluid applicator device 10 may be used in carrying out the step of depositing a sample in a receiving well of an electrophoretic gel as part of a method for assessing the level of specific lipoprotein particles present in a bodily fluid, as described in U.S. Patent Application Publication No. 2012/0052594, which is hereby incorporated by reference in its entirety. The exemplary method involves separating lipoprotein particles present in a bodily fluid sample by gel electrophoresis on a gel electrophoresis substrate, exposing the substrate to an antibody to detect an immunologically active agent associated with lipoprotein particles or components of lipoprotein particles, exposing the substrate to a reagent for detection of the presence of proteins or lipids, and determining the level of specific lipoprotein particles.

Kits including the fluid applicator device 10 described herein together with a system for gel electrophoresis are also contemplated. For example, a kit for gel electrophoresis may include an assembly, system, or apparatus, as described in U.S. Patent Application Publication No. 2012/0052594, which is hereby incorporated by reference in its entirety, and a fluid applicator device 10 as described herein.

Fluid applicator device 10 includes a handle 12, an applicator body 14, and applicator teeth 16(1), although fluid applicator device 10 may include other elements in other configurations. Handle 12 is used for manual or machine manipulation of fluid applicator device 10, as for example, described in U.S. Pat. No. 6,544,395, which is hereby incorporated by reference herein in its entirety. Handle 12 may have holes, notches, slots, protrusions, or other features that facilitate handling and alignment of fluid applicator device 10 for the sample loading and sample deposition procedures, as described further below.

Applicator body 14 is attached to handle 12 at planar surface 15 of applicator body 14. In one example, applicator body 14 is rigidly attached to handle 12 using adhesive or glue, although applicator body 14 may be mechanically attached to handle 12 by tabs or other fasteners. Applicator body 14 may be constructed of a metallized polymer, such as aluminized polyester or Mylar™. Use of the metalized polymer for the applicator body 14 provides a hydrophilic surface over the hydrophobic polymer. In one example, applicator body 14 may have a width from about 0.2 cm to 11.5 cm.

Applicator body 14 includes a number of applicator teeth 16(1) aligned along and extending longitudinally therefrom. The applicator teeth 16(1) may be distributed over the width of the applicator body 14. Although applicator body 14 is illustrated with twenty-eight applicator teeth 16(1), other numbers of applicator teeth 16(1) may be utilized. By way of example only, the fluid applicator device 10 may include a number of applicator teeth 16(1) in the range between 1 and 55, although the use of a higher number of applicator teeth 16(1) may be contemplated. In one example, fluid applicator device 10 includes at least (i.e., a minimum of) 20, 25, 30, 35, or 40 applicator teeth 16(1). In another example, fluid applicator device 10 includes up to (i.e., a maximum of) 45, 50, or 55 applicator teeth 16(1).

Applicator teeth 16(1) serve as an interface with sample wells and a sample substrate for deposition of a liquid sample on a substrate, as described further below. Each of the applicator teeth 16(1) is designed to carry and transfer a sample load of about 1 μl in the footprint of each tooth. The footprint consists of a one-dimensional (thin line) interface corresponding to the blade of the tooth that is about 5 mm long bounded on both sides by a gap of about 5 mm between each adjacent tooth, although the footprint may have other dimensions. Although fluid applicator device 10 is illustrated with applicator teeth 16(1), it is to be understood that fluid applicator device 10 could include applicator teeth with other configurations, such as applicator teeth 16(2)-16(7) as illustrated in FIGS. 2-7. Applicator device 10 may include various combinations of the configurations illustrated in FIGS. 2-7 located on the same applicator device 10 to permit variable depositions of the same or different fluid samples upon a selected substrate.

Referring again to FIG. 1, each of the applicator teeth 16(1) includes a base 18(1) and a tip 20(1). Each base 18(1) is located proximate to applicator body 14. Each of the applicator teeth 16(1) extends longitudinally from applicator body 14 along a length from base 18(1) to the tip 20(1), which is located distal to applicator body 14. In one example, at least one of the applicator teeth 16(1) includes a base 18(1) with a width greater than the tip 20(1) to facilitate sample loading, transfer, and deposition. In another example, each of the applicator teeth 16(1) includes base 18(1) with a width greater than the tip 20(1). The applicator teeth 16(1) may be formed in a variety of shapes that provide the configuration with base 18(1) with a width greater than the tip 20(1), including triangular shapes, curved shapes, boxed shapes, or a combination thereof, as illustrated in FIGS. 2-6 and described further below.

Referring now to FIGS. 2-7, the applicator teeth 16(2)-16(7) may include one or more perforations 22(2)-22(7) in various configurations, to modulate sample liquid retention and transfer, although other structures, such as apertures and/or notches, may be utilized to modulate sample liquid retention and transfer. Perforations 22(2)-22(7) in the applicator teeth 16(2-16(7) serve to control or facilitate liquid flow depending on the design. By way of example, as illustrated in FIGS. 2-7, perforations 22(2)-22(7) may be located lengthwise on the applicator tooth, width-wise, or a combination thereof. The perforations 22(2)-22(7) can be located at the top, middle, or bottom portion of each tooth, or possibly aligned down a central axis of the tooth. Each tooth may include a number of perforations 22(2)-22(7), all of consistent size and shape, or varying in size and shape. Applicator device 10 may include various combinations of the perforations 22(2)-22(7) in order to provide for variable depositions of the same or different samples on a selected substrate.

Figure 2:
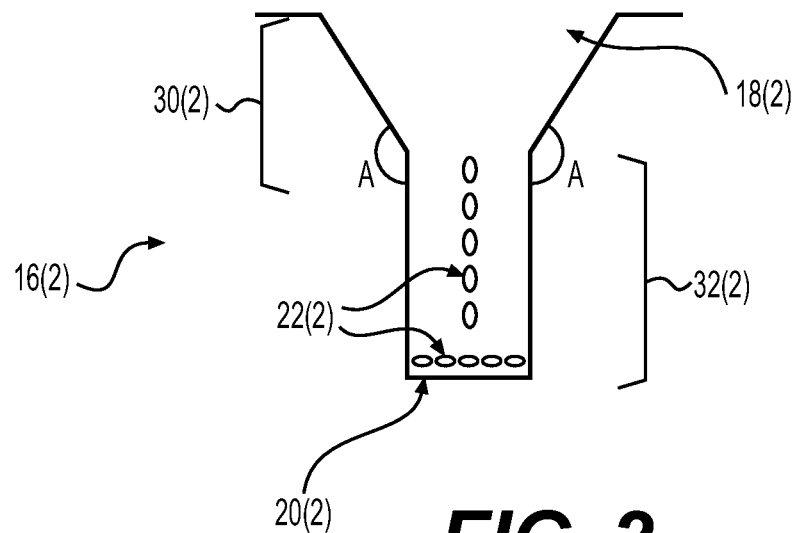
FIG. 2 is a side view of an embodiment of an individual tooth for use with the fluid applicator device of the present invention.

FIG. 2 is a side view of one embodiment of an applicator tooth 16(2) that may be utilized with fluid applicator device 10. Applicator tooth 16(2) includes a base 18(2) and a tip 20(2) that meet at obtuse angles A. In one example, the angles A are greater than or equal to about 110 degrees. The obtuse angles A promote fluid volume control by providing a surface to which a liquid sample will stick while limiting the length of the interface with the substrate. The applicator tooth 16(2) includes a tooth load section 30(2) near base 18(2). The tooth load section 30(2) has a width that tapers from base 18(2) toward the tip 20(2), but ending prior to tip 20(2). The applicator tooth 16(2) also includes a tooth delivery section 32(2) located near tip 20(2). The tooth delivery section 32(2) has a width that is about the same along its length. Applicator tooth 16(2) includes perforations 22(2) located along the central axis of the applicator tooth 16(2). Applicator tooth 16(2) also includes perforations 22(2) located near tip 20(2).

Figure 3:
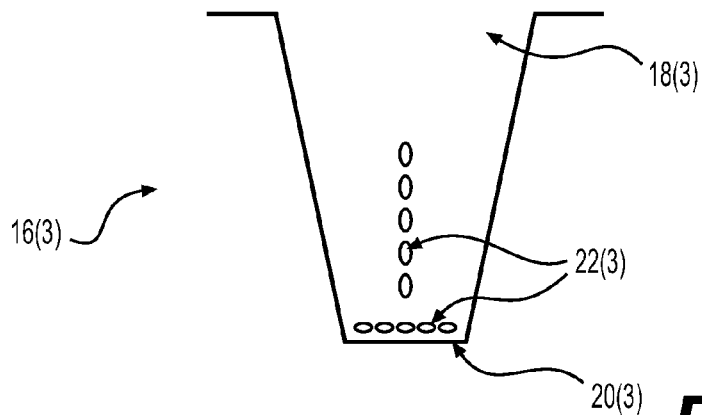
FIG. 3 is a side view of another embodiment of an individual tooth of the fluid applicator device of the present invention.
Figure 4:
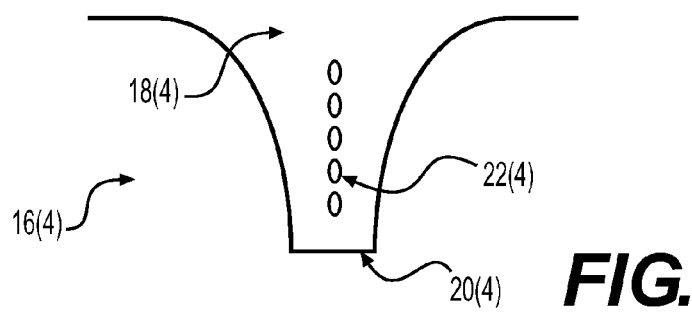
FIGS. 4, 5, and 6 are side views of alternative embodiments of an individual tooth for the fluid applicator device of the present invention.

FIG. 3 is a side view of an additional embodiment of an applicator tooth 16(3) that may be utilized with fluid applicator device 10. Applicator tooth 16(3) includes a base 18(3) and a tip 20(3), with the width of applicator tooth 16(3) tapering continuously in a straight line from base 18(3) to tip 20(3). Applicator tooth 16(3) includes perforations 22 located along the central axis of the applicator tooth 16(3). Applicator tooth 16(3) also includes perforations 22 located near tip 20(3). FIG. 4 is a side view of another embodiment of an applicator tooth 16(4) that may be utilized with fluid applicator device 10. Applicator tooth 16(4) includes a base 18(4) and a tip 20(4), with the width of applicator tooth 16(4) tapering continuously in a curved line from base 18(4) to tip 20(4). Applicator tooth 16(4) includes perforations 22(3) located along the central axis of the applicator tooth 16(4).

Figure 5:
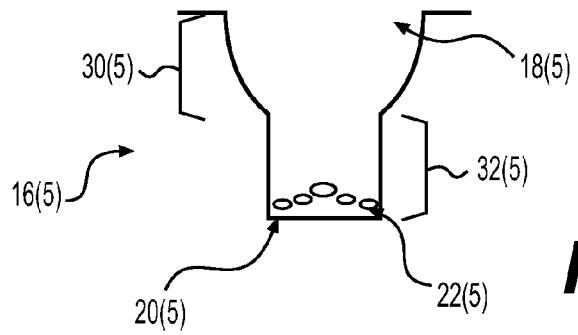

FIG. 5 is a side view of an additional embodiment of an applicator tooth 16(5) that may be utilized with fluid applicator device 10. Applicator tooth 16(5) includes a base 18(5) and a tip 20(5), with the width of applicator tooth 16(5) tapering discontinuously between the base 18(5) to tip 20(5). In this example, applicator tooth 16(5) includes a width defined by an edge comprising a curved and a straight surface. The applicator tooth 16(5) includes a tooth load section 30(5) near base 18(5). The tooth load section 30(5) has a width that tapers from base 18(5) toward the tip 20(5), but ending prior to tip 20(5). The applicator tooth 16(5) also includes a tooth delivery section 32(5) located near tip 20(5). The tooth delivery section 32(5) has a width that is about the same along its length. Applicator tooth 16(5) includes perforations 22(5) located near the tip 16(5) in an arc-shaped design, although other arrangements of the perforations are possible.

Figure 6:
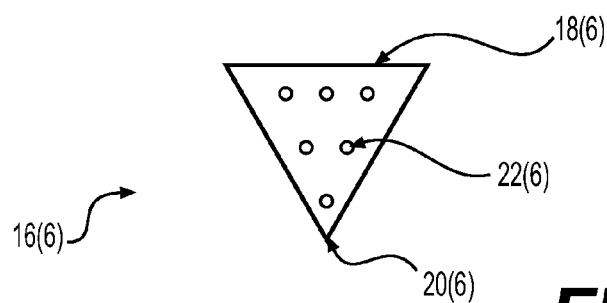

FIG. 6 is a side view of another embodiment of an applicator tooth 16(6) that may be utilized with fluid applicator device 10. Applicator tooth 16(6) includes a triangular body that extends between a base 18(6) and a tip 20(6). Applicator tooth 16(6) includes perforations 22(6) distributed about the triangular tooth body.

Figure 7:
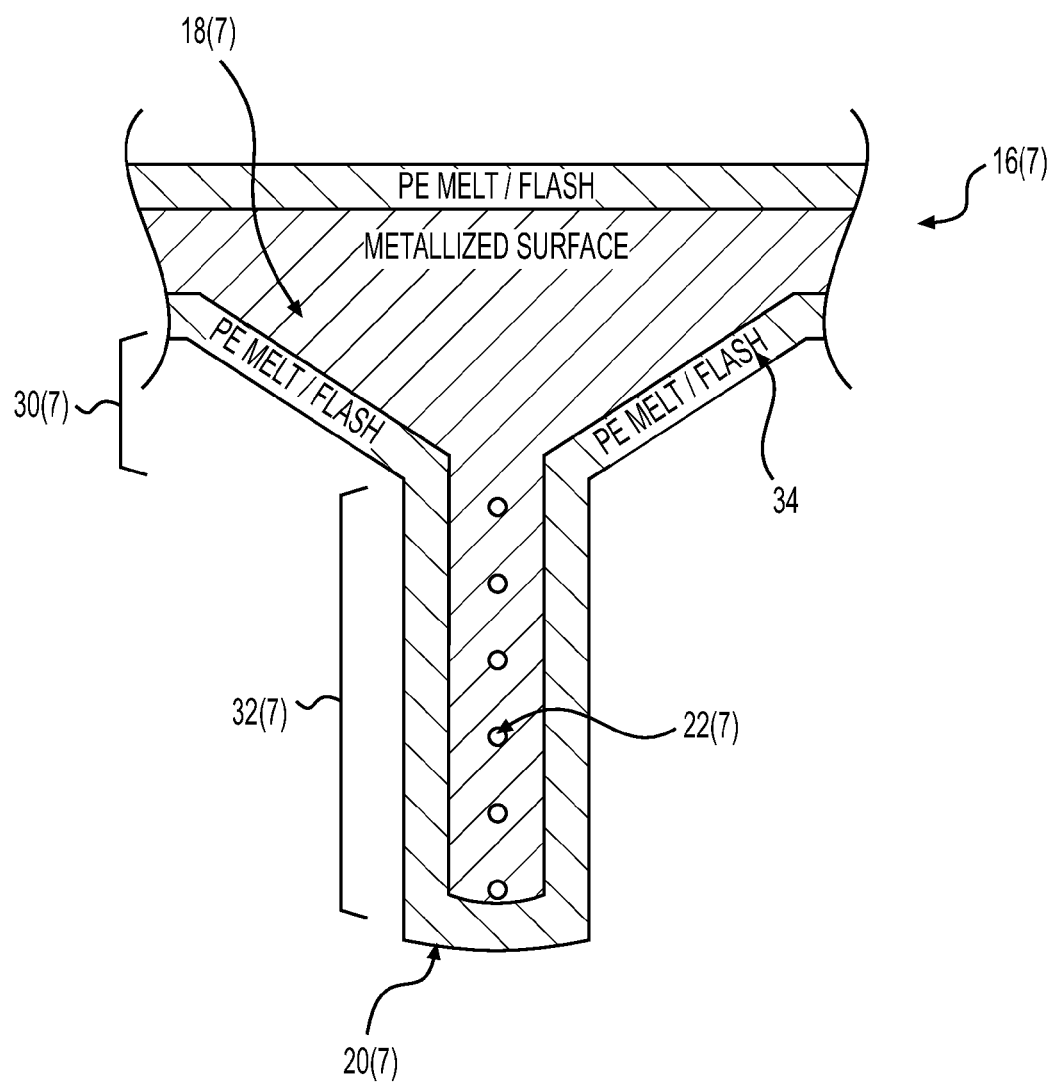
FIG. 7 is a side view of an embodiment of the individual tooth of the fluid applicator device of the present invention formed using laser cutting techniques.

Referring again to FIG. 1, the applicator teeth 16(1) may be formed in applicator body 14 using laser cutting, although other methods of forming the plurality of teeth 16(1), such a die-cutting, may be utilized. In one example, a combination of cutting methods, such as laser cutting and die cutting, may be used to create optimal surfaces on the applicator teeth 16(1) for liquid retention as described below. FIG. 7 shows an embodiment of an applicator tooth 16(7) formed by laser cutting of a metalized polymer. Applicator tooth 16(7) includes a base 18(7) and a tip 20(7) that meet at obtuse angles. In one example, the angles are greater than or equal to about 110 degrees. The obtuse angles promote fluid volume control by providing a surface to which a liquid sample will stick while limiting the length of the interface with the substrate. The applicator tooth 16(7) includes a tooth load section 30(7) near base 18(7). The tooth load section 30(7) has a width that tapers from base 18(7) toward the tip 20(7), but ending prior to tip 20(7). The applicator tooth 16(7) also includes a tooth delivery section 32(7) located near tip 20(7). The tooth delivery section 32(7) has a width that is about the same along its length. The dimensions between the tooth load section 30(7) and the tooth delivery section 32(7) controls delivery rate and the volume of sample applied. Applicator tooth 16(7) also includes perforations 22(7) located along the central axis of the applicator tooth 16(7).

Laser cutting melts the polymer around outside edges to create a flash 34 around the outside of the applicator tooth 16(7). In use with a fluid such as serum, the melted polymer (i.e. flash 34) is sufficiently hydrophobic to prevent serum from percolating off of the applicator tooth 16(7) when the liquid has sufficient surface area to adsorb on to the rest of the applicator tooth 16(7). The flash 34 maintains the fluid load on the surface of the applicator tooth 16(7) and prevents premature deposition or release of the fluid sample. In one example, the width of tip 20(7) of applicator tooth 16(7) is greater than or equal to the width of flash 34, and controls the dimension of fluid deposited on the substrate.

Another aspect of the present invention relates to a method for depositing a liquid sample on a substrate. The method involves providing a fluid applicator device comprising an applicator body having a surface that is generally planar. A plurality of aligned applicator teeth extend from said applicator body. Each applicator tooth extends longitudinally from said applicator body along a length from a base of the applicator tooth proximate to the applicator body to a tip of the applicator tooth distal to the applicator body. At least one applicator tooth of the plurality of aligned applicator teeth has a width that is greater at the base than at the tip. Each tooth of the applicator device is inserted into and removed from a supply volume of sample, thereby retaining a test volume of sample on each tooth. At least a portion of the test volume of sample is deposited onto a substrate by contacting the tips of the plurality of teeth of the fluid applicator device with the substrate.

Referring again to FIG. 1, in operation, the applicator teeth 16(1) are inserted into and removed from a sample reservoir including a fluid sample therein. The sample reservoir may contain any fluid sample for which electrophoresis testing is desired. The sample reservoir includes a supply volume of the fluid sample. The applicator teeth 16(1) retain a small portion, or a test volume, of the fluid sample on each tooth. In one example, each tooth is designed to carry and transfer a fluid sample load of about 1 µl. In one example, as illustrated in FIG. 7, the liquid sample adsorbs to the applicator teeth 16(7) by hydrogen bonding. The liquid sample is retained effectively by a combination of the flash 34 along the edges of the applicator teeth 16(2) and the perforations 22(7) along the central axis of the tooth body and at the tip 20(2).

Referring again to FIG. 1, next, at least a portion of the retained test volume of the fluid sample is deposited onto a substrate by contacting the tips 20(1) of the applicator teeth 16(1) of fluid applicator device 10 to the substrate. In one example, the substrate is an electrophoresis gel surface. Contacting the tips 20(1) causes the sample liquid retained on the applicator teeth 16(1) to come into contact with the substrate and disperses from the applicator teeth 16(1) a one-dimensional line on the substrate, equal to the interface dimension of tip 20(1) of each of the applicator teeth 16(1). In one example, as shown in FIG. 2, the relationship between the dimensions of the tooth load section 30(2) and the tooth delivery section 32(2) controls the delivery rate and the volume of the sample applied to the substrate.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A fluid applicator device comprising:
an applicator body; and
a plurality of aligned applicator teeth, each applicator tooth of said plurality of aligned applicator teeth extending longitudinally from said applicator body along a length from a base of the applicator tooth proximate to the applicator body to a tip of the applicator tooth distal to the applicator body, wherein at least one applicator tooth of said plurality of aligned applicator teeth has a width that is greater at the base than at the tip,
wherein one or more of said plurality of aligned applicator teeth comprises one or more perforations; and
wherein the one or more perforations are positioned along a center of at least one tooth of said plurality of aligned applicator teeth, and wherein the center extends along a length from the base to the tip of the at least one tooth of said plurality of aligned applicator teeth.

2. The fluid applicator device of claim 1, wherein each applicator tooth of said plurality of aligned applicator teeth has a width that is greater at the base than at the tip.

3. The fluid applicator device of claim 1, wherein the one or more perforations are positioned near the tip of each tooth of said plurality of aligned applicator teeth.

4. The fluid applicator device of claim 1, wherein the base of at least one tooth of said plurality of aligned applicator teeth and said applicator body meet at an obtuse angle.

5. The fluid applicator device of claim 1, wherein at least one tooth of said plurality of aligned applicator teeth further comprises:
a tooth load section near the base, wherein the width of the at least one tooth of said plurality of aligned applicator teeth in the tooth load section tapers along the length from the base toward the tip; and
a tooth delivery section near the tip, wherein the width of the at least one tooth of said plurality of aligned applicator teeth in the tooth delivery section is about the same along the length from the tip toward the base.

6. A fluid applicator device comprising:
an applicator body; and
a plurality of aligned applicator teeth, each applicator tooth of said plurality of aligned applicator teeth extending longitudinally from said applicator body along a length from a base of the applicator tooth proximate to the applicator body to a tip of the applicator tooth distal to the applicator body, wherein at least one applicator tooth of said plurality of aligned applicator teeth has a width that is greater at the base than at the tip,
wherein at least one tooth of said plurality of aligned applicator teeth further comprises:
a main tooth body surface covering a width of a central portion of the at least one tooth of said plurality of aligned applicator teeth and comprising a first surface material; and
a perimeter flash surface bordering said main tooth body surface at a perimeter of the at least one tooth of said plurality of aligned applicator teeth, wherein said perimeter flash surface comprises a second surface material, and wherein the second surface material is more hydrophobic than the first surface material.

7. The fluid applicator device of claim 6, wherein the first surface material is a metalized surface material.

8. The fluid applicator device of claim 6, wherein the second surface material is a polymer surface material.

9. The fluid applicator device of claim 6, wherein the width at the tip of the at least one tooth of said plurality of aligned applicator teeth is greater than about two times the width of said perimeter flash surface.

10. A method for depositing a liquid sample on a substrate, the method comprising:
providing a fluid applicator device comprising:
an applicator body having a surface that is generally planar; and
a plurality of aligned applicator teeth, each applicator tooth of said plurality of aligned applicator teeth extending longitudinally from said applicator body along a length from a base of the applicator tooth proximate to the applicator body to a tip of the applicator tooth distal to the applicator body, wherein at least one applicator tooth of said plurality of aligned applicator teeth has a width that is greater at the base than at the tip;

inserting and removing each tooth of said plurality of teeth of the fluid applicator device into a supply volume of sample, thereby retaining a test volume of sample on each tooth; and depositing at least a portion of the test volume of sample onto a substrate by contacting the tips of the plurality of teeth of the fluid applicator device with the substrate.

11. The method of claim 10, wherein the substrate is an electrophoretic substrate.

12. The method of claim 10, wherein each applicator tooth of said plurality of aligned applicator teeth has a width that is greater at the base than at the tip.

13. The method of claim 10, wherein one or more teeth of said plurality of aligned applicator teeth comprises one or more perforations.

14. The method of claim 13, wherein the one or more perforations are positioned along a center of at least one tooth of said plurality of aligned applicator teeth, and wherein the center extends along a length from the base to the tip of the at least one tooth of said plurality of aligned applicator teeth.

15. The method of claim 10, wherein the one or more perforations are positioned near the tip of each tooth of said plurality of aligned applicator teeth.

16. The method of claim 10, wherein at least one tooth of said plurality of aligned applicator teeth further comprises:
   a main tooth body surface covering a width of a central portion of at least one tooth of said plurality of aligned applicator teeth and comprising a first surface material; and
   a perimeter flash surface bordering said main tooth body surface at a perimeter of at least one tooth of said plurality of aligned applicator teeth, wherein said perimeter flash surface comprises a second surface material, and wherein the second surface material is more hydrophobic than the first surface material.

17. The method of claim 16, wherein the first surface material is a metalized surface material.

18. The method of claim 16, wherein the second surface material is a polymer surface material.

19. The method of claim 16, wherein the test volume of sample is proportional to the surface area of the first surface material.

20. The method of claim 16, wherein the perimeter flash surface has sufficient hydrophobicity to retain the volume of test sample on the at least one tooth following said inserting and prior to said depositing.

21. The method of claim 16, wherein the width at the tip of the at least one tooth of said plurality of aligned applicator teeth is greater than about two times the width of said perimeter flash surface.

22. The method of claim 16, wherein the width at the tip of the at least one tooth of said plurality of aligned applicator teeth defines a spot dimension of deposited test volume on the substrate.

23. The method of claim 10, wherein said fluid applicator device comprises 20 or more teeth.

24. The method of claim 10, wherein the base of at least one tooth of said plurality of aligned applicator teeth and said applicator body meet at an obtuse angle.

25. The method of claim 16, wherein at least one tooth of said plurality of aligned applicator teeth further comprises:
   a tooth load section near the base, wherein the width of the at least one tooth of said plurality of aligned applicator teeth in the tooth load section tapers along the length from the base toward the tip; and
   a tooth delivery section near the tip, wherein the width of the at least one tooth of said plurality of aligned applicator teeth in the tooth delivery section is about the same along the length from the tip toward the base.

26. The method of claim 25, wherein the dimension of the tooth load section to the dimension of the tooth delivery section determines the rate of said depositing and the volume of test sample applied to the substrate.

* * * * *